United States Patent
Phillips

(10) Patent No.: US 12,251,512 B2
(45) Date of Patent: Mar. 18, 2025

(54) PHYSIOLOGICALLY CONFORMABLE TRACHEAL TUBE

(71) Applicant: COVIDIEN LP, Mansfield, MA (US)

(72) Inventor: Matthew J. Phillips, Carlsbad, CA (US)

(73) Assignee: Covidien LP, Mansfield, MA (US)

( * ) Notice: Subject to any disclaimer, the term of this patent is extended or adjusted under 35 U.S.C. 154(b) by 909 days.

(21) Appl. No.: 17/344,573

(22) Filed: Jun. 10, 2021

(65) Prior Publication Data

US 2021/0393906 A1   Dec. 23, 2021

Related U.S. Application Data

(60) Provisional application No. 63/040,876, filed on Jun. 18, 2020.

(51) Int. Cl.
*A61M 16/04* (2006.01)
*A61M 16/08* (2006.01)

(52) U.S. Cl.
CPC .... *A61M 16/0434* (2013.01); *A61M 16/0465* (2013.01); *A61M 16/0816* (2013.01); *A61M 2207/00* (2013.01)

(58) Field of Classification Search
CPC .............. A61M 16/04; A61M 16/0465; A61M 16/0434; A61M 25/10; A61M 16/08; A61M 16/0816; A61M 16/0445
See application file for complete search history.

(56) References Cited

U.S. PATENT DOCUMENTS

| | | | | |
|---|---|---|---|---|
| 3,034,510 A * | 5/1962 | Kittel | ................. | A61M 25/005 604/101.01 |
| 4,498,473 A * | 2/1985 | Gereg | ............... | A61M 16/0418 128/207.14 |
| 5,554,119 A * | 9/1996 | Harrison | ........... | A61M 16/0481 604/101.05 |
| 5,832,920 A * | 11/1998 | Field | ................. | A61M 16/0463 128/207.14 |
| 6,527,739 B1 * | 3/2003 | Bigus | ................ | A61M 25/1002 604/101.01 |
| 6,716,236 B1 * | 4/2004 | Tzeng | ...................... | A61F 7/12 607/113 |

(Continued)

OTHER PUBLICATIONS

Kulstad, E., et al. (2013). Induction, maintenance, and reversal of therapeutic hypothermia with an esophageal heat transfer device. Resuscitation, 84(11), 1619-1624. https://doi.org/10.1016/j.resuscitation. 2013.06. (Year: 2013).*

*Primary Examiner* — Samchuan C Yao
*Assistant Examiner* — Mishal Zahra Hussain

(57) ABSTRACT

A tracheal tube include a conformable conduit that forms a respiratory passage to transfer respiratory gases to a patient. A helical inflatable lumen is formed in or on an interior surface of the conformable conduit. Fluid transferred into the helical inflatable lumen causes the inflatable lumen to assume an expanded configuration to expand an outer diameter of the conformable conduit relative to an unexpanded configuration of the helical inflatable lumen. When in the expanded configuration and inserted in a patient, conformable walls of the conformable conduit expand outwards to contact the tracheal walls such that the conformable conduit is self-sizing to a patient's trachea size.

14 Claims, 11 Drawing Sheets

(56) References Cited

U.S. PATENT DOCUMENTS

| | | | |
|---|---|---|---|
| 7,766,871 B2 * | 8/2010 | Hirszowicz | A61M 25/1011 |
| | | | 604/103.07 |
| 8,568,438 B2 * | 10/2013 | Burbank | A61F 5/56 |
| | | | 128/207.18 |
| 8,813,750 B2 * | 8/2014 | O'Neil | A61M 16/0427 |
| | | | 128/207.14 |
| 2010/0313895 A1 | 12/2010 | O'Neil et al. | |
| 2020/0306474 A1 * | 10/2020 | Flaherty | A61F 5/56 |

* cited by examiner

PHYSIOLOGICALLY CONFORMABLE TRACHEAL TUBE

CROSS-REFERENCE TO RELATED APPLICATIONS

The present application claims the priority to and the benefit of U.S. Provisional Application No. 63/040,876, entitled "PHYSIOLOGICALLY CONFORMABLE TRACHEAL TUBE" and filed on Jun. 18, 2020, the disclose of which is incorporated by reference in its entirety herein.

BACKGROUND

The present disclosure relates generally to tracheal tubes that have a collapsible/expandable structure and that can expand to conform to a patient's anatomy.

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the course of treating a patient, a tube or other medical device may be used to administer a fluid (e.g., air, oxygen, medication) into the patient's airway. For example, airway devices, such as oropharynx cannulas (e.g., endotracheal tubes, tracheal tubes) and nasopharynx cannulas (e.g., tubes for nasal intubation), may be used to facilitate flow of one or more fluids into or out of the patient. Accordingly, such airway devices provide a flow passage between the patient's airway and the environment surrounding the patient (e.g., a gas source, a monitor). These airway devices may be part of a breathing circuit that allows a physician to facilitate breathing assistance or mechanical ventilation of the patient.

Airway devices are sized to the patient, with larger diameter tubes used for adult patients, while smaller diameter tubes are used for pediatric patients. Accordingly, airway tubes may come in a range of sizes that reflect a diameter (e.g., an outer diameter) of the airway tube. These airway tubes are typically slightly smaller than the airway passage to permit manipulation and advancement of the airway tube within the airway during insertion. Accordingly, many cuffs include an inflatable cuff to bridge a gap and provide a seal between the outside of the airway tube or device and the patient's airway passage to close the breathing circuit so that a ventilator can control the pressure of the air flowing into the patient's lungs.

SUMMARY

Certain embodiments commensurate in scope with the originally claimed subject matter are summarized below. These embodiments are not intended to limit the scope of the disclosure. Indeed, the present disclosure may encompass a variety of forms that may be similar to or different from the embodiments set forth below.

In one embodiment, a tracheal tube is provided that includes a conformable conduit forming a respiratory passage sized to transfer respiratory gases to a patient. The tracheal tube also includes a spiral, e.g., helical, inflatable lumen formed in or on an interior surface of the conformable conduit, wherein the helical inflatable lumen is closed at a distal end such that fluid transferred into the helical inflatable lumen causes the helical inflatable lumen to expand in diameter, causing the conformable conduit to assume an expanded configuration. The tracheal tube also includes a connector coupled to a proximal end of the conformable conduit in fluidic communication with the respiratory passage. The respiratory passage of the conformable conduit is fluidically isolated from the helical inflatable lumen.

In one embodiment, a system includes a tracheal tube. The tracheal tube a conformable conduit forming an airway lumen to transfer respiratory gases to a patient and an inflatable lumen formed in or on an interior surface of the conformable conduit, wherein the inflatable lumen forms a spiral or helix about the interior surface, and wherein the inflatable lumen is closed at a first end such that fluid transferred into the inflatable lumen from a second end causes the conformable conduit to assume an expanded configuration to expand an outer diameter of the conformable conduit relative to an unexpanded configuration of the conformable conduit. The system also includes an inflation controller configured to adjust inflation of the inflatable lumen by transferring inflation fluid to or from the inflatable lumen, the inflation controller comprising a memory and a processor configured to execute instructions stored in the memory, the instructions causing the inflation controller to: receive a pressure measurement indicative of a pressure of the inflatable lumen; and adjust the pressure of the inflatable lumen based on the pressure measurement.

In an embodiment, a method includes the steps of providing a conformable conduit comprising an inflatable lumen arranged in a spiral about an interior surface of the conformable conduit; notching the inflatable lumen at a location between a proximal end and a distal end of the inflatable lumen to access an interior space of the inflatable lumen; and coupling an inflation connector to the notched inflatable lumen at a first end of the inflation connector such that the inflation connector is fluidically coupled to the interior space of the inflation lumen, the inflation connector comprising a valve at a second end.

In an embodiment, a method of administering therapeutic hypothermia includes the steps of transferring respiratory gases to a patient via a respiratory passage of a conformable conduit; and transferring cooled fluid to a helical inflatable lumen formed in or on an interior surface of the conformable conduit to cause the helical inflatable lumen to expand in diameter, causing the conformable conduit to assume an expanded configuration, wherein the respiratory passage is fluidically isolated from the helical inflatable lumen, and wherein the cooled fluid has a lower temperature than a temperature of the respiratory gases.

Features in one aspect or embodiment may be applied as features in any other aspect or embodiment, in any appropriate combination.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

Figure 1:
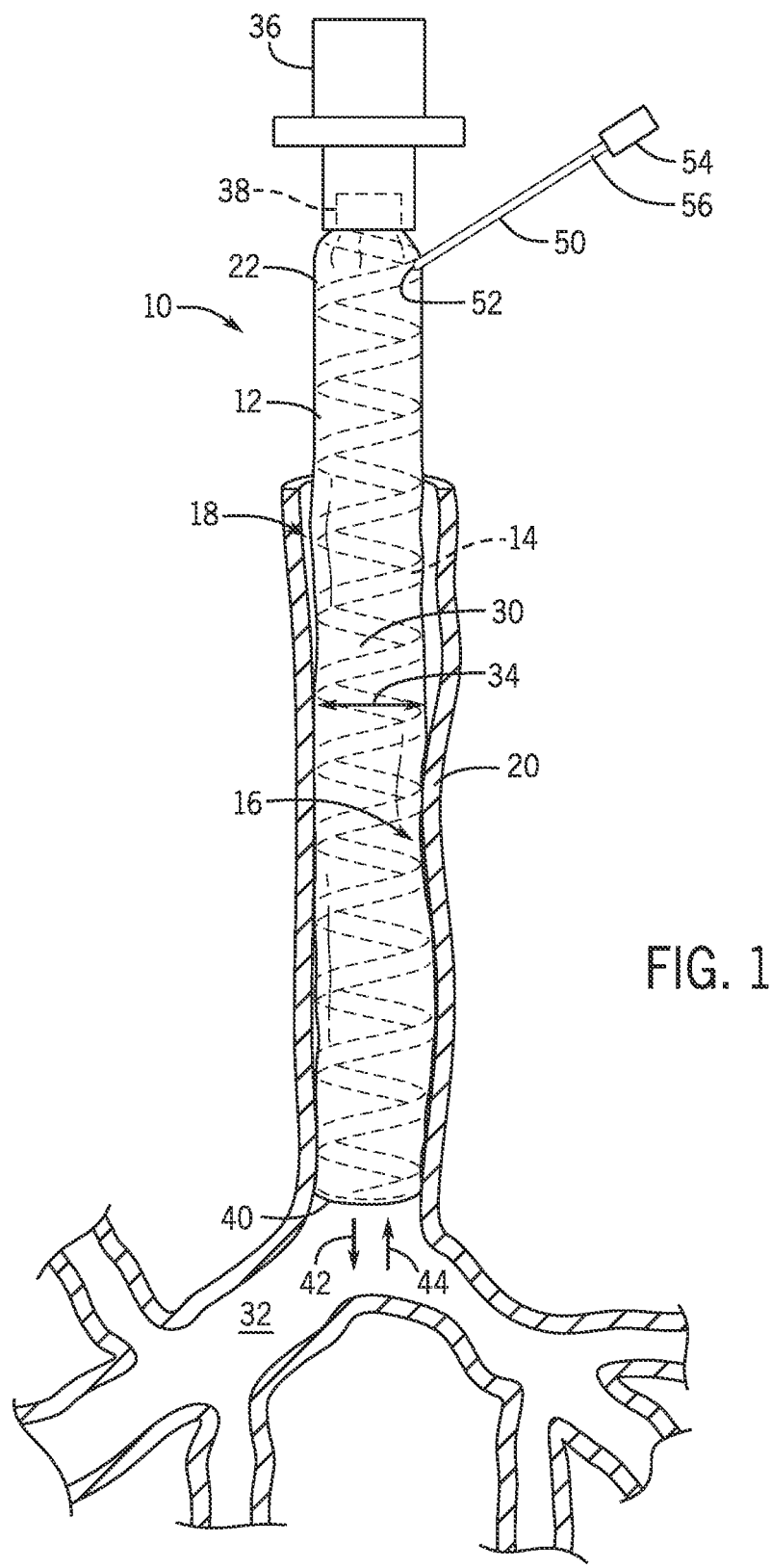
FIG. 1 shows a physiologically conformable tracheal tube including a conformable conduit and a helical inflatable lumen in an expanded configuration according to embodiments of the present disclosure.

Provided herein are physiologically conformable tracheal tubes that are collapsible and/or expandable and that can transition between collapsed and expanded configurations to self-size to a patient's anatomy. The physiologically conformable tracheal tubes as disclosed herein provide improved sealing by expanding to conform to the individual contours of a patient's airway.

Conventional endotracheal tubes are formed with relatively thick walls that provide structural rigidity and that support the tracheal tube during insertion and placement. Such tracheal tubes have a fixed outer diameter that is generally slightly smaller than the patient's airway to permit insertion into the trachea. Further, because of the relatively thick and rigid walls of such tracheal tubes, the tracheal tube inner diameter that forms the gas pathway is yet smaller, resulting in greater work of breathing for a ventilated patient. Caregivers select a tracheal tube that is estimated to be a best fit for the patient from a set of fixed diameter tracheal tubes, balancing ease of insertion and rapid intubation of smaller diameters with a desire for an airway diameter that is as large as possible. Conventional tracheal tubes, in order to maintain sufficient stiffness and axial force to advance into the airway during intubation and maintain an open airway during ventilation, sacrifice flexibility that would aid steering into the trachea. These relatively stiff tracheal tubes do not conform to the patient's tracheal tissue, and they may include an inflatable cuff that expands to bridge the gap between the outer diameter of the tracheal tube and the tracheal walls to create a closed breathing circuit. However, the cuff may become dislodged by patient movement or coughing, which may compromise the seal. Further, secretions that build up on the cuff are regularly suctioned, which adds to the complexity of patient care.

The physiologically conformable tracheal tubes of the present techniques provide certain advantages over conventional tracheal tubes. The tracheal tubes disclosed herein include a conformable conduit having a collapsible wall that folds in on itself in a collapsed configuration during intubation, and expands to fill the trachea in an expanded configuration during ventilation. The conformable conduit wall is thinner than and less rigid than conventional tracheal tubes. In addition, the conformable tracheal tube as provided herein includes an inflatable lumen that is arranged in a spiral (e.g., helical) about the conformable conduit of the tracheal tube. Inflation of the inflatable lumen applies force to the wall of the conformable conduit, causing the wall of the conformable conduit to expand outwardly. In use during ventilation, the conformable conduit can expand to make direct contact with the tracheal passage. Accordingly, in the expanded configuration, the conformable conduit of the tracheal tube has an inner diameter forming the respiratory gas pathway that is substantially the size of the patient's own airway passage. This results in less work of breathing for a ventilated patient because the respiratory gas pathway of the tracheal tube is almost the same as the native physiology in the trachea.

In addition, the physiologically conformable tracheal tubes as provided herein permit sealing along the points of contact with the tracheal wall. Because the conformable conduit is longer than a conventional tracheal cuff, this results in a longer seal. Further, in an embodiment, the contact pressure may be lower than that of a conventional tracheal cuff, permitting effective airway sealing in a more comfortable manner for the patient. The inflatable lumen generates hoop stresses in the tracheal tube, which contribute to the lateral force that forms the seal. However, the intervening conformable walls of the conformable conduit, at regions between coils of the helix, permit axial flexibility. This axial flexibility may improve the conformance of the tracheal tube to the airway, which in turn may help maintain the tracheal tube position during patient-generated movement of the airway, such as coughing, even at a lower contact pressure against the patient's airway.

The physiologically conformable tracheal tubes of the present disclosure can be inserted into a patient, e.g., during intubation, in a collapsed configuration. In an embodiment, structural support for insertion in the collapsed configuration is provided by an intubation guide or bougie. The tracheal tube can be collapsed around the guide or bougie and then expanded when inserted to an appropriate position in the airway. Accordingly, the collapsed tracheal tube is a smaller diameter structure relative to a conventional tracheal tube, and thus may be easier to manipulate within the airway. Further, because the tracheal tube can transition between expanded and collapsed positions based on an inflation level of the helical inflatable lumen, the tracheal tube can be collapsed to remove the airway seal to permit spontaneous breathing trials for a patient without removing the tracheal tube from the airway.

While the disclosed embodiments are discussed in the context of tracheal tubes such as endotracheal tubes or tracheostomy tubes, it should be understood that the physiologically conformable tubes that are collapsible and/or expandable may be part of or used in conjunction with other airway devices or as part of a breathing circuit including connected devices. As non-limiting examples, the physiologically conformable tubes may be utilized with a feeding tube, an endotracheal tube, an endobronchial tube, a tracheostomy tube, an introducer, an endoscope, a bougie, a circuit, an airway accessory, a connector, an adapter, a filter, a humidifier, a nebulizer, a nasal cannula, or a supraglottic mask/tube.

FIG. 1 shows a physiologically conformable tracheal tube 10 with a conformable conduit 12 that is in an expanded configuration. The tracheal tube 10 includes an inflatable lumen 14 that, in the illustrated embodiment, is part of or coupled to an interior surface 16 of the conformable conduit 12 and that is arranged in a helix or spiral configuration extending along at least a portion of the conformable tube 12. In the expanded configuration, the inflatable lumen 14 is at least partially inflated to cause expansion of the conformable conduit 12 such that an exterior surface 18 of the conformable conduit 12 directly contacts and applies pressure to tracheal walls 20 of the patient's airway. In an embodiment, the conformable conduit 12 includes one or more conformable walls 22, such as a cylindrical or curved wall. The conformable walls 22 may be generally oversized relative to the airway such that the tracheal tube 10 can self-size to the airway and expand until a desired pressure against the tracheal walls 20 is reached. In the expanded configuration, the conformable conduit 12 forms a respiratory passage 30 for the passage of respiratory gases into the lower airway 32. To promote elongated seal formation via the direct contact of the exterior surface 18 with the tracheal walls 20, the inflatable lumen 14 is positioned on the opposing interior surface 16 such that the exterior surface 18 presents a smooth sealing face. However, in certain embodiments, the inflatable lumen 14 may be positioned on the exterior surface 18 or may be integrated within the conformable wall or walls 22.

The respiratory passage inner diameter 34 in the expanded configuration conforms to the patient airway along its length. The outer diameter of the conformable conduit 12 is the distance of the inner diameter 34 together with a thickness of relatively thin wall 22 of the conformable conduit 12. In contrast to conventional tracheal tubes with a fixed inner and outer diameter, the conformable conduit 12 is capable of expanding different amounts (expanding fully in some spots and less fully in other spots) and thereby assuming different diameters at different points along its length (e.g., along an airway flow axis through the proximal end 38 and the distal end 40) to narrow and widen along with any contours in the tracheal walls 22. Further, variability in patient anatomy may also result in the same-sized tracheal tube 10 being expanded to different diameters within different patients in use.

The tracheal tube 12 may include a coupled resilient tracheal tube connector 36, such as a standard 15 mm connector, that can couple to ventilator tubing. In the illustrated embodiment, the interior surface 16 at a proximal end 38 of the conformable conduit 12 is directly coupled to the tracheal tube connector 36. However, other arrangements are also contemplated (see FIG. 7). Respiratory gases received via the tracheal tube connector 36 are transferred out of or back into a distal end 40 of the conformable conduit 12 as part of inhalation (arrow 42) and exhalation (arrow 44).

The inflatable lumen 14 includes or is coupled to an inflation connector 50 that facilitates inflation. The inflation connector 50 may be an extending portion of the inflatable lumen 14 or a separate conduit connected to the inflatable lumen 14 and fluidically coupled to the inflatable lumen 14. The inflation connector 50 extends away from the conformable conduit 12 at a first distal end 52 positioned at or near the tracheal tube 12 to permit access by a caregiver and terminates at a valve 54 at a second proximal end 56. The inflation connector 50 may couple to a device that transfers inflation fluid into and/or out of the inflatable lumen 14. The inflation device may be a manual inflation device, such as a syringe, operated by a caregiver, or may be an automatic inflation controller such as a motor or pump (see FIG. 12).

Figure 2:
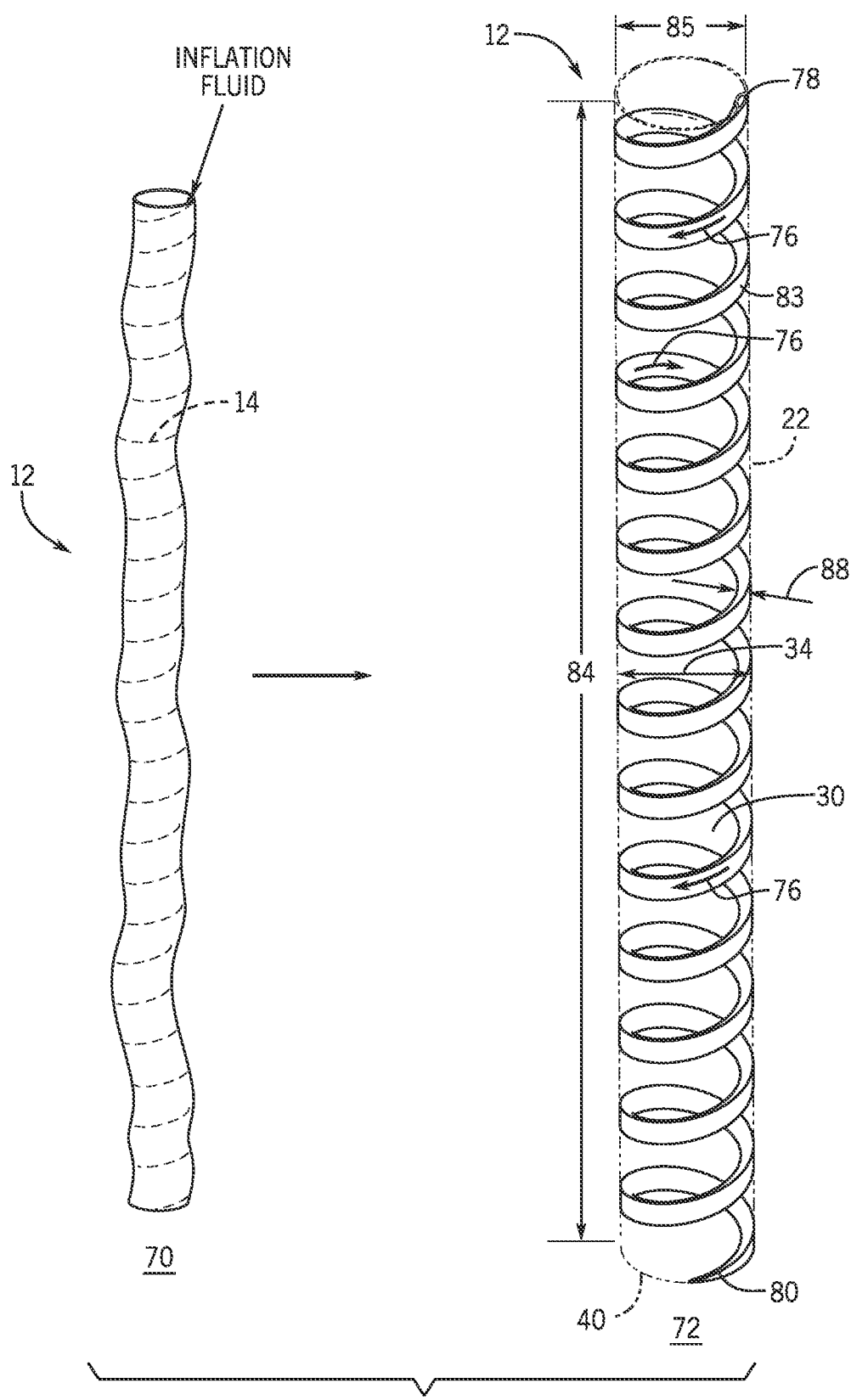
FIG. 2 shows a transition between a collapsed configuration and an expanded configuration of the physiologically conformable tracheal tube according to embodiments of the present disclosure.

As provided herein, the expansion of the conformable conduit 12 is accomplished by inflation of the inflatable lumen 14. As inflation fluid, such as ambient air, is transferred into the inflatable lumen 14, the inflatable lumen 14 opens and fills, expanding its helical shape outward. As the helical shape grows in diameter, it brings the conformable walls 22 with it correspondingly, to cause the conformable conduit 12 to assume the expanded configuration. FIG. 2 shows a transition from an example collapsed configuration 70 to an example expanded configuration 72, which accompanies a transition of the inflatable lumen 14 from an uninflated state to an inflated state. It should be understood that the reverse transition is also covered by the disclosed embodiments, and the tracheal tube 10 can transition between the expanded configuration 72 and the collapsed configuration 70 via deflation of the inflatable lumen 14. Further, the expanded configuration 72 may refer to an operating expanded configuration in the patient or outside of the patient, and may be fully or partially expanded. In a fully expanded state outside of the patient, the conformable conduit 12 is expanded via inflation of the inflatable lumen 14 to a plateau volume at pressures just below rupture.

Transfer of fluid to inflate the inflatable lumen 14, shown by arrows 76, causes the helical form of the inflatable lumen 14 to attempt to straighten as the internal volume increases, which causes the lumen 14 to expand outward. In an embodiment, the inflatable lumen 14 is isolated at both ends from the breathing circuit as well as fluidically isolated from the ambient environment, with a proximal end 78 closed by valve 54 and a sealed distal end 80. Accordingly, the inflatable lumen 14 is fluidically isolated from the respiratory passage 30 of the conformable conduit 12. The helix of the inflatable lumen 14, which is coupled to the wall 22 of the conformable conduit 12, cannot freely straighten, but instead expands during inflation to cause individual coils 83 of the helix to move away from one another and to increase in diameter. This results in movement of opposing side of the walls 22 away from each other to increase the inner diameter 34 as well as an increase in a length dimension (84) as the wall 22 unfolds to permit expansion.

In an embodiment, the maximum diameter (inner diameter 34 or an outer diameter) of the tracheal tube 10 represents a fully expanded configuration in which the conformable conduit 12 is expanded outside of a patient or other passage. The caregiver may select an appropriate tracheal tube 10 from a set of differently-sized tracheal tubes 10 that is a closest match to an estimated patient trachea size. In an embodiment, the appropriate size tracheal tube 10 is estimated to be oversized (in its fully expanded configuration) relative to the patient trachea, in order to provide ample material to contact the patient's tracheal walls. When inserted into the patient to a desired contact pressure with the tracheal walls 20, the conformable walls 22 may include one or more folds at certain points along the exterior surface 18, because the tracheal walls 20 prevent additional expansion to the fully expanded inner diameter 34. In an embodiment, the conformable conduit 12 has a fully expanded or maximum inner diameter 34 or fully expanded maximum outer diameter 85 of at least 7.5 mm, at least 10 mm, at least 12 mm, at least 15 mm, at least 20 mm, at least 25 mm, or at least 30 mm.

As provided herein the inflatable lumen 14 is arranged in a helix that extends along at least a portion of a length of the inflatable conduit 12 between the proximal end 38 and the distal end 40. The helix may be distributed along at least 50% of the length dimension (along arrow 84) of the conformable conduit 12 in the expanded configuration 72 in an embodiment. The helix may be a left-handed or right-handed helix.

The helix has an inner diameter 88 when fully or mostly inflated that is relatively small compared to the maximum or operating (in-use within the patient) inner diameter 34 of the respiratory passage 30. In an embodiment, the inflatable lumen 14, in the expanded configuration 72, has an inner diameter 88 of less than 3 mm, less than 2 mm, or less than 1 mm. In an embodiment, the inner diameter 88 of the inflatable lumen 14 is less than 20%, less than 5% or less than 1% the inner diameter 34 of the conformable conduit in the expanded configuration 72. This arrangement provides the advantage of minimal encroachment of the inflatable lumen 14 into the respiratory gas flow path and is in contrast to other types of expanding structures (such as internal sleeves) that may cause the wall 22 to buckle or prolapse inward. The helical shape tends to expand outward during inflation, which causes opposing sides of the wall 22 to pull away from each other, thus preventing a prolapsed region. Further, the inflatable lumen 14, in use and when at least partially inflated, applies outward radial hoop stresses oriented towards the tracheal walls.

Figure 3:
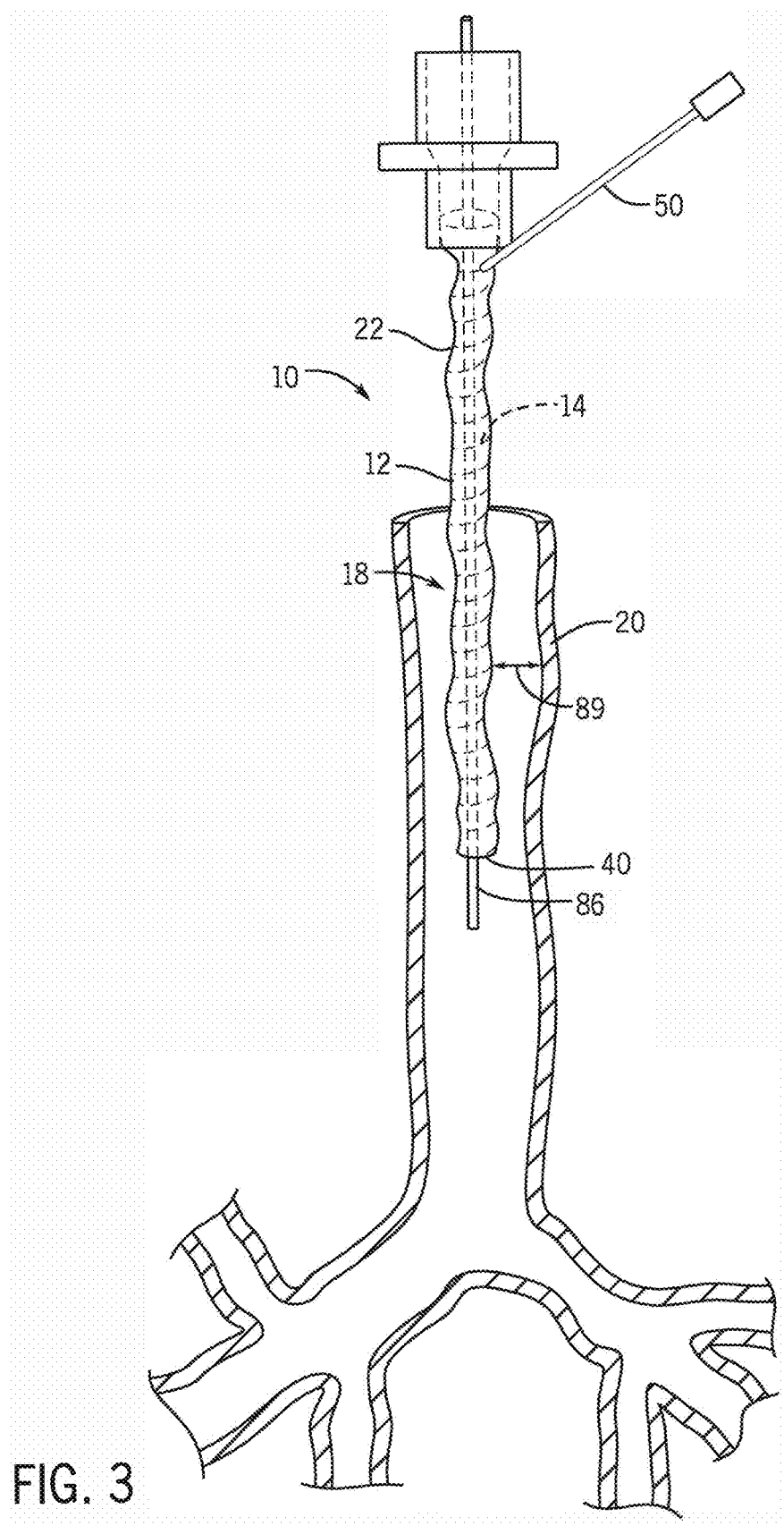
FIG. 3 shows a physiologically conformable tracheal tube in a collapsed configuration according to embodiments of the present disclosure.

FIG. 3 shows the tracheal tube 10 in the patient airway in the collapsed configuration (e.g., collapsed configuration 70, FIG. 2) in which the inflatable lumen 14 is in an uninflated state and mostly or entirely empty of fluid. In the illustrated embodiment, a guide 86 is inserted within the tracheal tube 10, extending beyond the distal end 40, and the wall 22 of the conformable conduit 12 is folded around the guide 86. The guide 86 provides structural rigidity to the tracheal tube 10 to aid insertion or removal. As shown, in the collapsed configuration, the exterior surface 18 forms a gap 89 with the tracheal walls because the profile of the tracheal tube 10 is reduced in the collapsed configuration. Once properly positioned, the inflatable lumen 14 can be inflated via the inflation connector 50 to cause a transition to the expanded configuration (see FIG. 1), and the guide 86 is removed. As provided herein, the tracheal tube 10 can be collapsed by a caregiver by manually or automatically removing inflation fluid from the inflatable lumen 14 to cause the inflatable lumen 14 to transition from a mostly or fully inflated state to an uninflated state. For example, the tracheal tube 10 can be collapsed in advance of removal or during spontaneous breathing trials. When fluid is removed from the inflatable lumen 14, the pressure against the helix coils of the lumen is reduced, and the helix coils relax back toward each other into a tighter, curved position, retracting the conformable walls 22 with them and reducing the overall diameter of the tube.

Figure 4:
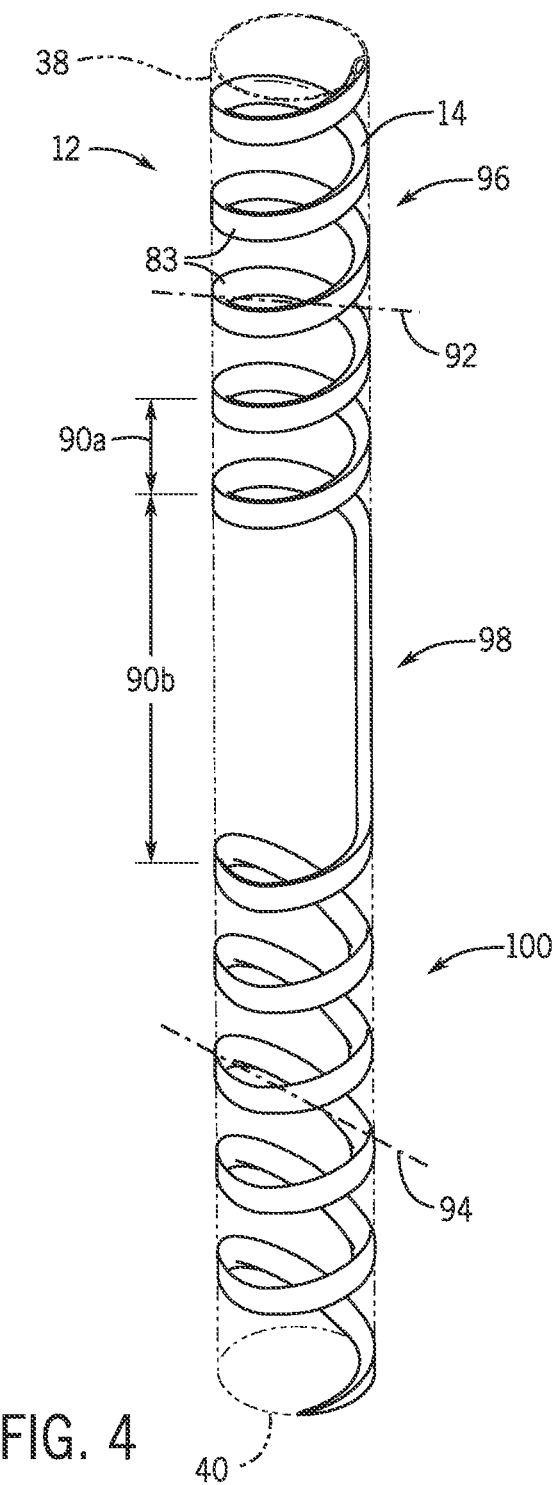
FIG. 4 shows features of the helical arrangement of the inflatable lumen of a physiologically conformable tracheal tube according to embodiments of the present disclosure.
Figure 5:
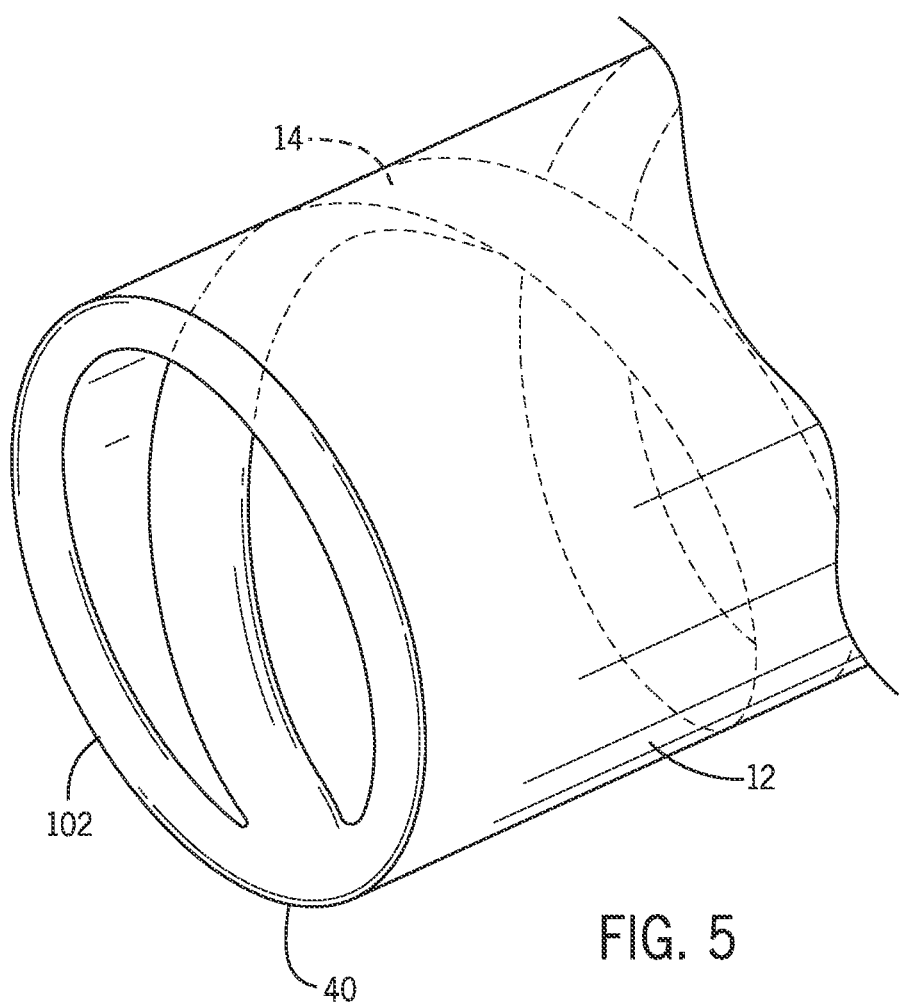
FIG. 5 shows an embodiment of a physiologically conformable tracheal tube in which the inflatable lumen terminates in an annulus at a distal end according to embodiments of the present disclosure.

As illustrated in FIG. 4, the helix arrangement or spiral may be characterized by a pitch indicative of a distance between the individual coils 83. In an embodiment, the pitch may be regular or irregular. Further, different sections may have regular pitches that are different from one another. The pitch may be selected to be relatively smaller (pitch 90a) in areas in which more axial stiffness is desired and relatively larger (pitch 90b) in areas in which more flexibility is desired. The helix may also be characterized by a fully expanded coil diameter 92, which may be constant or variable along the conformable conduit 12. The helix may further be characterized by a pitch angle 94, which influences the angle of the hoop stresses. One or more of the pitch, coil diameter, and pitch angle may be selected to achieve desired flexibility or stiffness in the conformable conduit 12. In an embodiment, the helix of the inflatable lumen 14 may be arranged to create a higher stiffness region 96, a lower stiffness region 98, and an intermediate stiffness region 100. FIG. 5 illustrates an embodiment in which the inflatable lumen 14 terminates in an annulus 102 about the distal end 40 of the conformable conduit 12 to stabilize the distal end 40 when in the expanded configuration 72. Additionally or alternatively, the conformable conduit 12 may include an annulus at other locations, such as an annulus closer to the proximal end at a location corresponding to the epiglottis of the patient to seal out secretions associated with infection.

In one example, the pitch 90 between individual coils 83 may be about 5 mm-300 mm. In one example, the fully expanded coil diameter 92 may be at least 7.5 mm, at least 10 mm, at least 12 mm, at least 15 mm, at least 20 mm, at least 25 mm, or at least 30 mm. In on example, the pitch angle may be between 0 and 60 degrees (positive or negative tilt).

Figure 6:
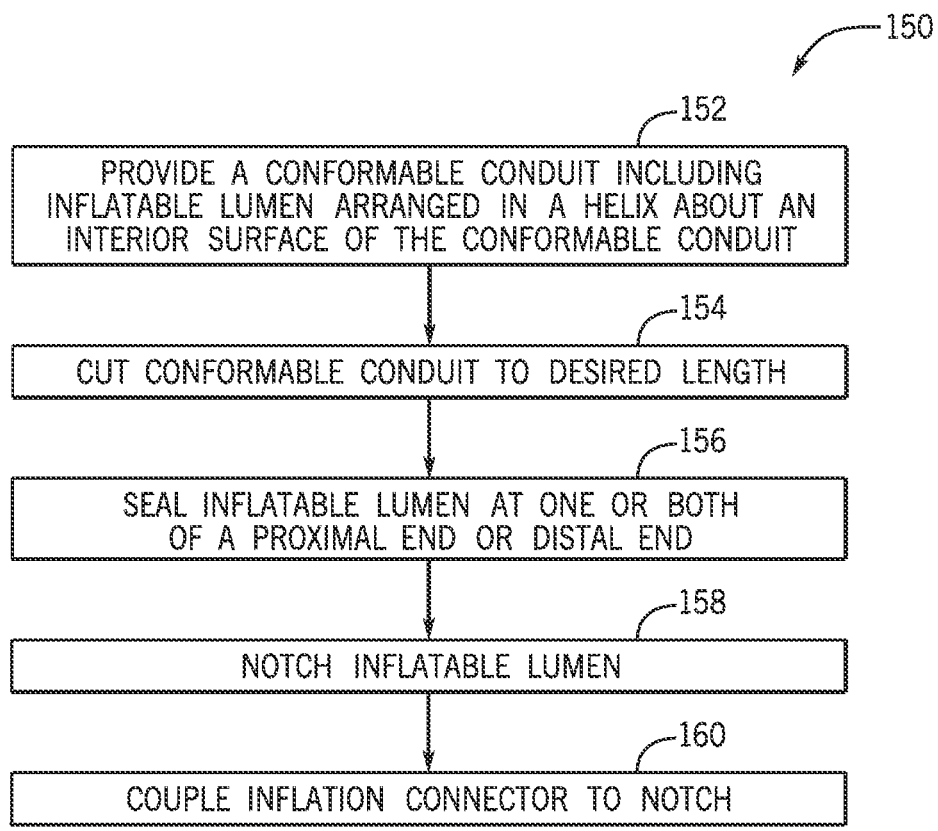
FIG. 6 is a flow diagram of a method of manufacturing a physiologically conformable tracheal tube including a conformable conduit and a helical inflatable lumen according to embodiments of the present disclosure.

With the above understanding of the components of the tracheal tube 10 in mind, further discussion is provided herein regarding an example process of forming or manufacturing the tracheal tube 10. FIG. 6 is a flow diagram of a method 150 of manufacturing or forming the tracheal tube 10 and includes various steps or actions represented by blocks. It should be noted that the method 150 may be performed as a manufacturing process by a single system or by separate systems/devices.

The method 150 includes the step of providing the conformable conduit 12 with the inflatable lumen disposed about the interior surface (block 152). In an embodiment, the conformable conduit 12 can be extruded, e.g., extrusion blow-molded, or molded as an integrally formed structure with the inflatable lumen 14. In one example, a wire is coiled into a helix as part of an extrusion process, and removal of the wire after setting of the extruded tube provides a structure of the inflatable lumen 14. In this manner, the manufacturing of the conformable conduit 12 and the inflatable lumen 14 may be relatively less complex relative to mechanically expanding structures with components that expand by sliding or actuating at pivot points. Further, the conformable conduit 12 and the inflatable lumen 14 may be formed from a single material. In another embodiment, the conformable conduit 12 may be formed as a separate component, and the inflatable lumen may be applied (e.g., adhered) in a helix arrangement to the already-formed conformable conduit 12 as a subsequent step.

In processes in which the conformable conduit 12 is formed as part of a longer tube, such an extrusion, the method includes a step of cutting the conformable conduit 12 to a desired length (block 152). The method may also use heat as part of the cutting or as a separate step to seal ends of the inflatable lumen (block 154) to facilitate fluidic isolation of the inflatable lumen 14. To provide an inflation access point, a notch may be formed in the inflatable lumen, e.g., at a location along the conformable conduit between the proximal and distal ends of the inflatable lumen (block 156) and an inflation connector 50 is inserted into or otherwise coupled to the notch (block 158). In an alternate arrangement, the inflatable lumen 14 may not have a separately coupled inflation connector, and the method 150 may not include a notch formation step.

One or both of the walls 22 of the conformable conduit 12 and the inflatable lumen 14 may be made of a polyurethane or polyurethane-based composition having suitable mechanical and chemical properties. An example of a suitable polyurethane is Dow Pellethane® 2363-90A. In other embodiments, the conformable conduit 12 and/or the inflatable lumen 14 are made of other suitable polymeric compositions. Examples of suitable polymeric compositions include polymethylmethacrylate (PMMA), polyacrylonitrile (PAN), polyamide (such as nylon) (PA), polycarbonate (PC), polyesters (such as polyethylene terephthalate (PET)), polyolefins (such as polyethylenes (PE) and polypropylenes (PP)), polystyrene (PS) or vinyls (such as polyvinyl chloride (PVC) and polyvinylacetate), or silicone rubber. Other polymers and/or polymer admixtures having suitable mechanical, chemical, and biocompatibility properties may also be used.

The conformable conduit 12 and/or the inflatable lumen 14 may be formed with walls sufficiently thin to fold in on themselves in order to conform to a patient tracheal diameter. The thickness and/or material composition of the wall of the conformable conduit 12 and the inflatable lumen 14 may be the same or different. In an embodiment, the wall of the conformable conduit 12 and/or the inflatable lumen 14 walls is between 10 microns and 3 millimeters in thickness. In an embodiment, the wall 22 of the conformable conduit 12 is less than 100 μm.

Figure 7:
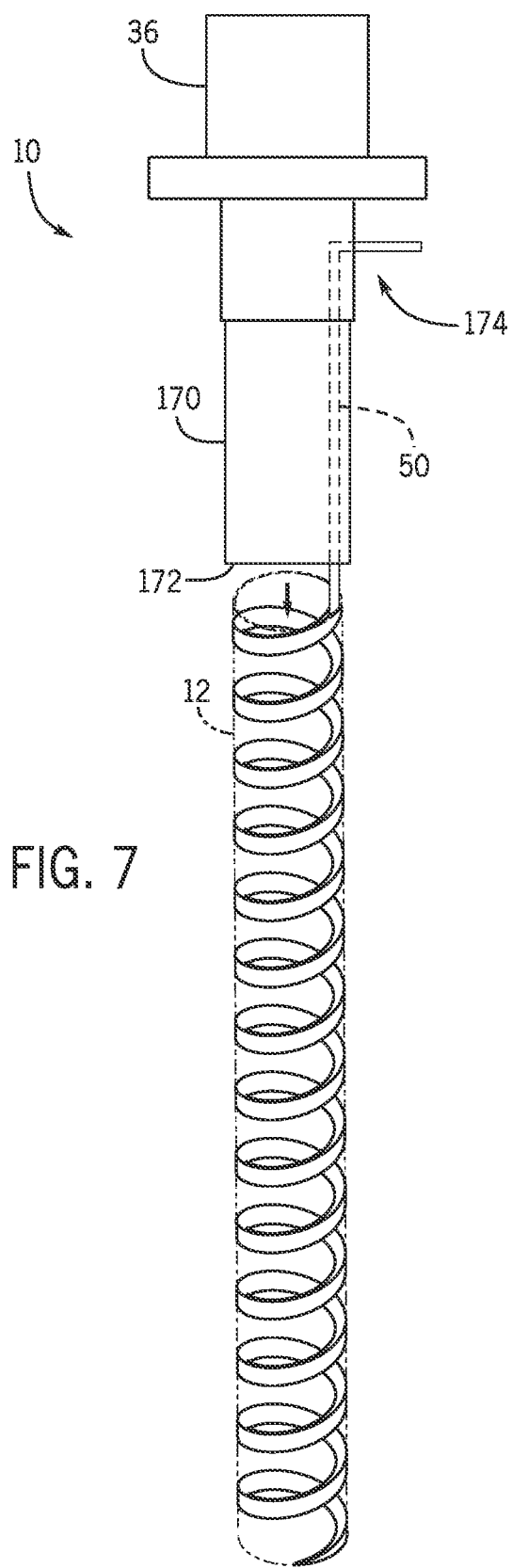
FIG. 7 shows an arrangement of an inflation connector portion coupled to the inflatable lumen according to embodiments of the present disclosure.

FIG. 7 illustrates an embodiment in which the tracheal tube 10 includes a resilient adapter 170 that is positioned between the tracheal tube connector 36 and the conformable conduit 12. The resilient adapter 170 may be integrally formed or coupled to the tracheal tube connector 36. The conformable tube 12 is coupled to a distal portion 172 of the resilient adaptor 170. The resilient adapter 170 provides additional axial stiffness during insertion within a patient's upper airway, may provide a handle for manipulation of the tracheal tube 14 to couple and uncouple breathing circuit components, and may also separate the conformable conduit 12 from a patient's teeth during use.

The inflation connector 50 may be routed on or in the tracheal tube connector 36 and, when present, the resilient adapter 170. As illustrated in FIG. 7, the inflation connector 50 may be routed from the conformable conduit 12 and proximally into the body of the resilient adapter 170 to exit from a side wall 174 of the tracheal tube connector 36.

Figure 8:
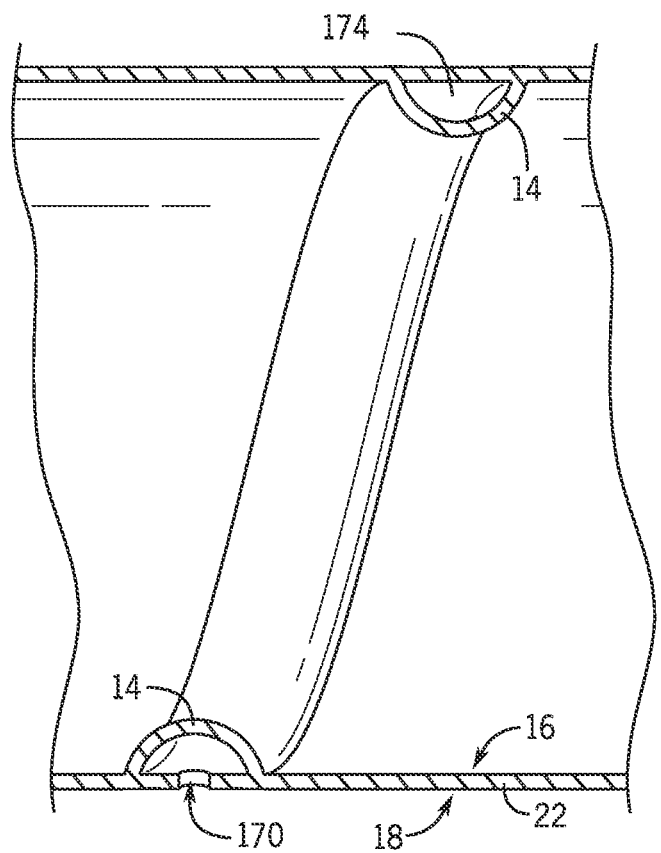
FIG. 8 is a cross-sectional view of a physiologically conformable tracheal tube including a notch formed through a wall of the conformable conduit to access an interior space of the inflatable lumen according to embodiments of the present disclosure.
Figure 9:
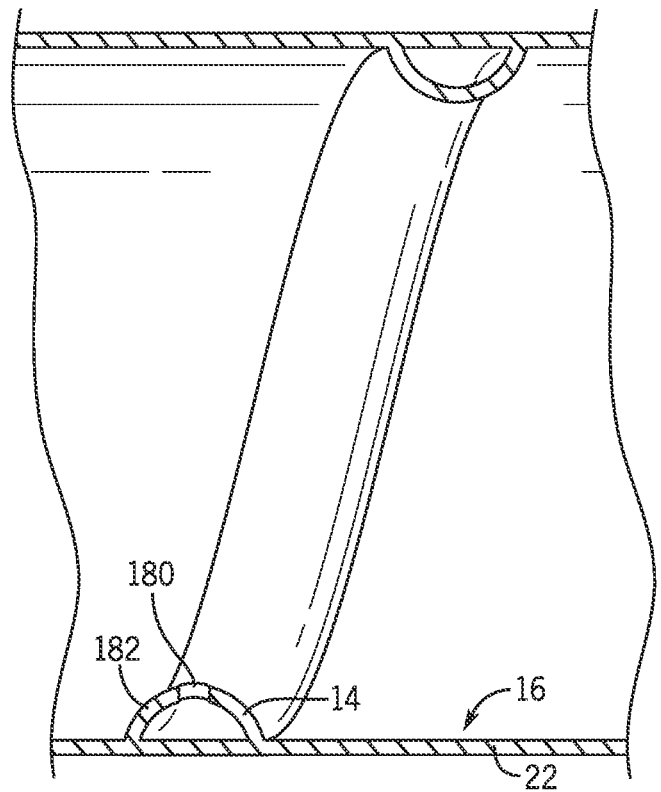
FIG. 9 is a cross-sectional view of a physiologically conformable tracheal tube including a notch formed through an interior wall of the inflatable lumen to access an interior space of the inflatable lumen according to embodiments of the present disclosure.
Figure 10:
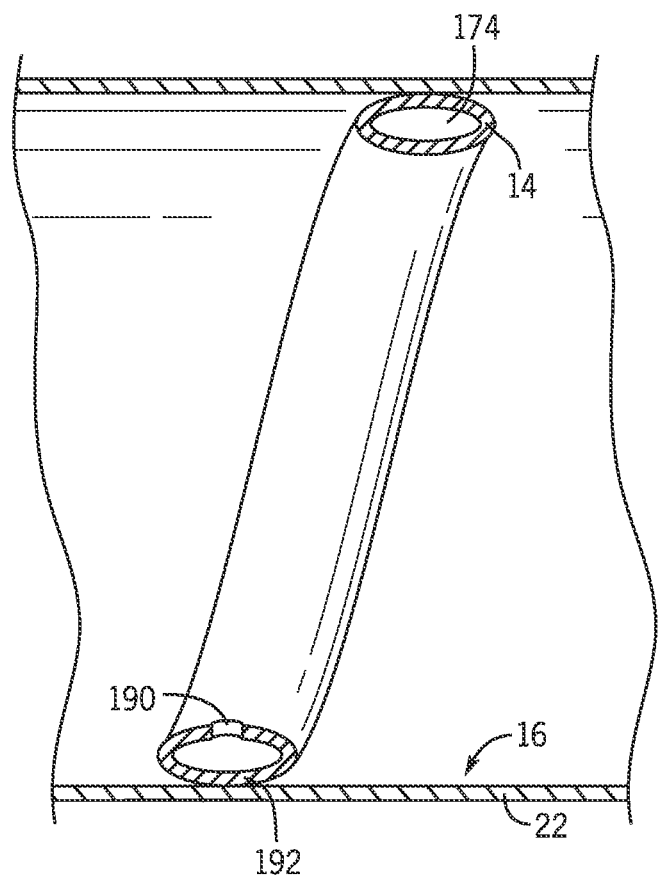
FIG. 10 is a cross-sectional view of a physiologically conformable tracheal tube including a notch formed through a wall of the conformable conduit and a wall of the inflatable lumen to access an interior space of the inflatable lumen according to embodiments of the present disclosure.
Figure 11:
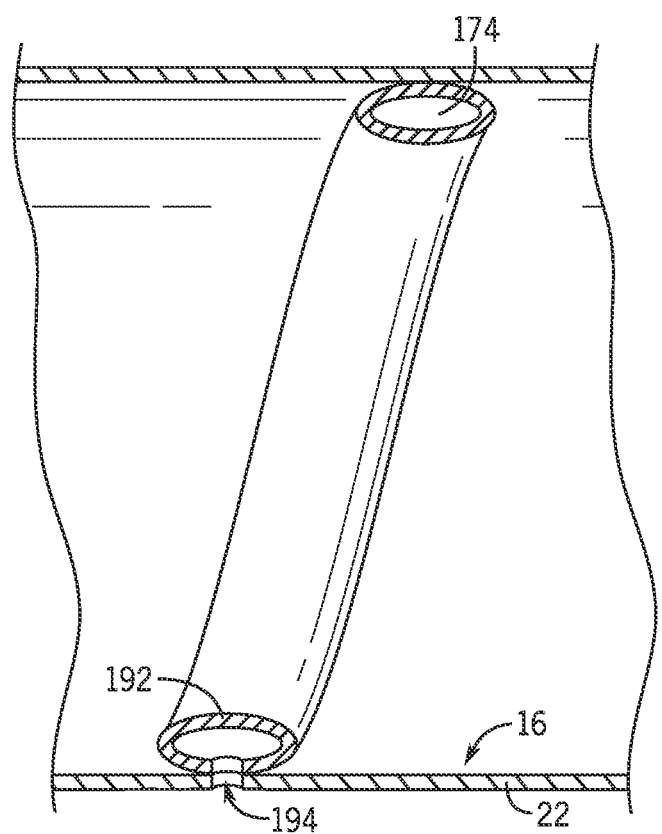
FIG. 11 is a cross-sectional view of a physiologically conformable tracheal tube including a notch formed through an interior wall of the inflatable lumen to access an interior space of the inflatable lumen according to embodiments of the present disclosure.

FIGS. 8-11 show cross-sectional views of various embodiments of arrangements of a notched inflatable lumen 14. The inflatable lumen 14 may be integrally formed or extruded with the conformable conduit, e.g., of a same material. In FIG. 8, the inflatable lumen 14 is formed as a dome protruding from the interior surface 16 such that the wall 22 of the conformable conduit 12 is part of the inflatable lumen 14. A notch through the wall 22 permits the inflation connector (see FIG. 1) to access an interior space 174. In FIG. 9, a notch 180 is formed through a wall portion 182 of the inflatable lumen 14 that protrudes from the interior surface 16 to access the interior space 174. Alternatively, the inflatable lumen 14 may be a separate component that is adhered to the interior surface 16. As shown, a notch 190 may by formed on an only a wall 192 of the inflatable lumen 14 (FIG. 10) or may be a notch 194 cut through both the wall 192 and the wall 22 of the conformable conduit 12.

Figure 12:
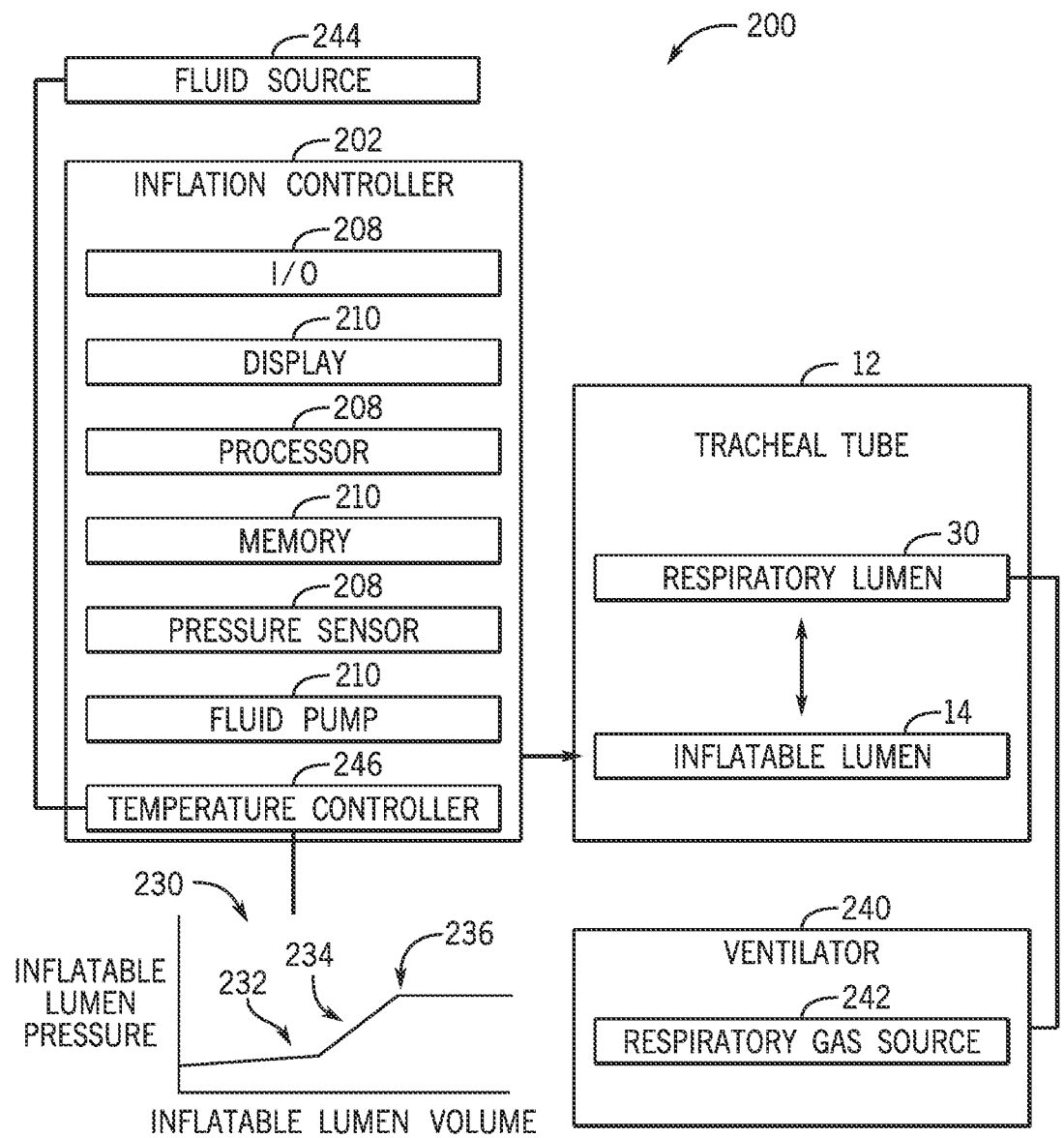
FIG. 12 is a block diagram of a system including a physiologically conformable tracheal tube and an inflation controller according to embodiments of the present disclosure.

FIG. 12 is a block diagram of a system 200 of controlling pressure in the inflatable lumen 14 to establish or maintain appropriate sealing of the conformable conduit 12 with the airway when inserted in the patient. The inflatable lumen 14 is fluidically coupled to an inflation controller 202 that adjusts an internal pressure of the inflatable lumen 14 based on instructions executed by a processor 204 and stored in a memory 206. The processor 204 may include one or more application specific integrated circuits (ASICs), one or more general purpose processors, one or more controllers, one or more programmable circuits, or any combination thereof. The memory 206 may include volatile memory, such as random access memory (RAM), and/or non-volatile memory, such as read-only memory (ROM). The memory 206 also include stored instructions, code, logic, and/or algorithms that may be read and executed by the processor 204 to perform the techniques disclosed herein.

The processor 204 receives feedback from a pressure sensor 208 fluidically coupled to the inflatable lumen 14 (e.g., positioned in the inflatable lumen 14, within a housing of the inflation controller 202, or at a location between the inflatable lumen and the inflation controller 202, e.g., coupled the valve 54 or intervening tubing) and, based on detected deviations from preset target pressures, adds or removes fluid from the inflatable lumen 14 via a fluid pump 210. In an embodiment, the internal pressure of inflation lumen is set to be 10 psi or less or set to 5 psi or less. An operator may adjust preset targets for inflatable lumen pressure using input/output devices 212, and the inflation controller 202 can provide notifications of deviations and pressure adjustment on a display 212. The caregiver may provide inputs via user-selectable buttons, touch screen sensors on the display 212, or other mechanical or capacitive buttons or keys on the inflation controller 202 to convey user inputs that are provided to the processor 204.

The conformable conduit 12 and/or the inflatable lumen 14 may be formed from one or more materials that facilitate high volume, low pressure expansion. In an embodiment, such materials are associated with an applied pressure to the tracheal walls 20 that is related to a pressure within the inflatable lumen 14. In an embodiment, the pressure within the respiratory passage 30 has a positive linear relationship with the pressure applied to the tracheal walls 20, such that increases in pressure within the inflatable lumen 14 cause a corresponding increase in pressure applied by the conformable conduit 12 to the tracheal walls 20.

In an embodiment, the inflation controller 202 adjusts pressure within the inflation lumen 14 based on inflation characteristics at various pressures within the inflation lumen 14. In the illustrated example, a compliance curve 230 characteristic of an example inflation lumen 14 shows multiple inflation phases within the inflation lumen. High volume low pressure materials may be characterized with a first inflation stage in which transfer of inflation fluid causes a relatively slow and steady linear volume and pressure relationship as the inflatable lumen fills to a certain volume. As shown in the compliance curve 230, has a first inflection point 232 at a transition between the first stage and a second stage in which increasing pressure and interior volume has a relatively shallow slope compared to the inflation characteristics after the inflection point 232.

The inflation controller 202 may be configured to adjust the internal pressure of the inflatable lumen 14 based on feedback from the pressure sensor to keep the pressure in a range on the steeper linear part 234 of the compliance curve 230 that is after the first inflection point 232 and that represents a more rapid change in pressures responsive to changes in volume and vice versa. Further, the inflation controller 202 may be configured to identify changes in slope of pressure vs. time of the interior pressure of the inflatable lumen 14 to identify inflections points and associated states of the compliance curve 230. Volumes in the inflatable lumen 14 past a second inflection point 236 may be associated with undesirable pressures and overinflation.

Inflation of the inflatable lumen 14 at pressure below the first inflection point 232 achieves full or partial expansion and removal or reduction of a wrinkled configuration. After the first inflection point 232, the pressure increases on patient anatomy and further expansion. At the second inflection point 236, there may be maximum expansion achieved. After the second inflection point 236, a third stage is stretching of the inflation lumen 14 diametrically. Effective sealing of the conformable conduit 12 may start at pressures associated with the first inflection point 232. By keeping the pressures of the inflatable lumen 14 in the steeper linear part 234 of the compliance curve 230, effective sealing pressures are maintained.

The compliance curve 230 may be specific to a particular size and material composition of the tracheal tube 12 and may be determined empirically to estimate the target pressure ranges of the inflatable lumen 14. Accordingly, the inflation controller 202 may store calibration information related to a number of available sizes or configurations of the tracheal tube 10. The appropriate identification information may be used to select the corresponding compliance curve 230.

Respiratory gas pressure from a ventilator 240 delivering respiratory gases into a respiratory passage 30 of the tracheal tube 10 from a respiratory gas source 242 may also cause changes to the applied pressure to the tracheal walls. The inflation controller 202 may be configured to receive ventilation parameter information from the ventilator 240 (or may be integrated into a unitary device with the ventilator 240) and dynamically adjust the pressure in the inflatable lumen 14 accordingly. For example, the pressure in the inflatable lumen 14 during inhalation vs. exhalation may be different. Inhalation gas flow may apply greater outward pressure to the walls 22 of the conformable conduit 12 and the inflatable lumen 14. The inflation controller 202 may be programmed to dynamically adjust the pressure in the inflatable lumen 14 over a course of a breathing cycle to keep the pressure in the target range and at a target applied pressure to the tracheal walls 20. In an embodiment, the tracheal tube 10 applies pressure of 30 cm $H_2O$ or less, 20 $H_2O$ or less, or 15 $H_2O$ or less to the tracheal walls 20.

The fluid within the inflatable lumen 14 is transferred or removed via the fluid pump 210. Because the fluid is fluidically isolated from the breathing circuit, the transferred fluid from a fluid source 244 may be ambient air or from a nonsterile or nontreated fluid source. In an embodiment, the fluid source 244 is coupled to a temperature controller 246 that heats or cools the fluid according to instructions of the inflation controller 202. The temperature controller 246 may include heating or cooling elements to adjust a temperature of the fluid transferred into the inflatable lumen 14 as well as a thermistor fluidically coupled to the inflatable lumen 14 to monitor the inflatable lumen internal temperature.

Figure 13:
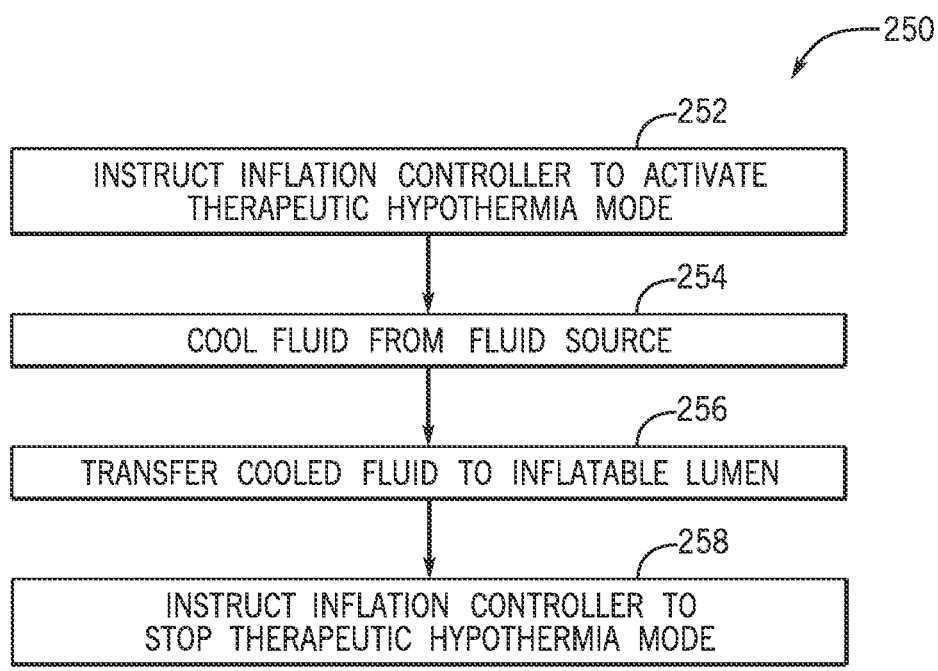
FIG. 13 is a flow diagram of a method of administering therapeutic hypothermia using the physiologically conformable tracheal tube according to embodiments of the present disclosure.

In an embodiment, the inflatable lumen 14 may be used to administer therapeutic hypothermia, as shown in the flow diagram of FIG. 13. Because the conformable conduit 12 forms a seal directly against the tracheal walls 20, cool air within the inflatable lumen 14 may operate to cool the tissue and lower a patient local or general temperature. Further, because of the fluidic isolation between the inflatable lumen 14 and the respiratory passage, the conformable conduit 12 can be used to cool the esophageal tissue more than the breathing gas due to conduction (direct contact between the helix of the inflatable lumen 14 and the esophageal walls), to promote cooling of the esophagus and not cooling of the breathing gas. In this manner, the breathing gases can be humidified and heated to temperatures that are well-tolerated by the lungs, while the walls 22 of the conformable conduit 12 act as a local heat sink.

In the method 250, instructions are provided to the inflation controller that a therapeutic hypothermia mode is activated (block 252). The instructions trigger the fluid source 244 to cool a fluid (block 254) under control of the temperature controller 246. In an embodiment, the fluid may be cooled to temperatures of 23-34° C. to administer therapeutic hypothermia, and the temperature in the inflatable lumen 14 is monitored by the temperature controller, which may be coupled to a thermistor. The cooled fluid is transferred into the inflatable lumen 14 (block 256), which may involve first removing warmer fluid from the inflatable lumen 14. The method 250 may also include a setting to stop the therapeutic hypothermia mode (block 258). This may include stopping periodic fluid exchange within the inflatable lumen 14 to replace fluid warmed by the patient tissue to maintain a desired internal temperature. At a stop of the method 250, the inflation controller 250 may exchange the cooled fluid with warmer fluid or may monitor the eventual warming of the fluid within the inflatable lumen 14 to tissue temperature via direct contact.

In an embodiment, the inflatable lumen 14 may be implemented as a loop to include a return flow path from a distal-to-proximal direction to permit warmed fluid from the distal end to return via the flowpath and be continuously replaced by cooler fluid. Accordingly, the inflatable lumen 14 may include a return helical coil or a return linear path from the distal end 40 to the proximal end 38.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims. Further, it should be understood that certain elements of the disclosed embodiments may be combined or exchanged with one another.

What is claimed is:

1. A tracheal tube comprising:
    a conformable conduit forming a respiratory passage sized to transfer respiratory gases to a patient;
    a helical inflatable lumen formed in or on an interior surface of the conformable conduit, wherein the helical inflatable lumen is closed at a distal end such that fluid transferred into the helical inflatable lumen causes the helical inflatable lumen to expand in diameter, causing the conformable conduit to assume an expanded configuration, wherein the helical inflatable lumen terminates in an annulus encircling a distal end of the conformable conduit; and a connector coupled to a proximal end of the conformable conduit in fluidic communication with the respiratory passage, wherein the respiratory passage is fluidically isolated from the helical inflatable lumen.

2. The tracheal tube of claim 1, wherein the helical inflatable lumen comprises a connector portion that extends out of and away from the conformable conduit and that is fluidically coupled to a proximal portion of the helical inflatable lumen.

3. The tracheal tube of claim 2, wherein the connector portion comprises a valve.

4. The tracheal tube of claim 1, wherein the conformable conduit has a wall thickness of 100 µm or less.

5. The tracheal tube of claim 1, wherein the conformable conduit comprises nylon, polyvinylchloride, silicone rubber, or polyurethane.

6. The tracheal tube of claim 1, wherein the conformable conduit and the helical inflatable lumen are formed of a same material.

7. The tracheal tube of claim 1, wherein the tracheal tube comprises an endotracheal tube or a tracheostomy tube.

8. The tracheal tube of claim 1, wherein the connector is a 15 mm connector.

9. The tracheal tube of claim 1, wherein the helical inflatable lumen comprises a right-handed or a left-handed helix.

10. The tracheal tube of claim 1, wherein the helical inflatable lumen has at least one section having an irregular pitch along a length of the conformable conduit.

11. The tracheal tube of claim 1, wherein the helical inflatable lumen is configured to be cooled, relative to a temperature of the respiratory gases, by the fluid transferred into the helical inflatable lumen.

12. The tracheal tube of claim 1, wherein the helical inflatable lumen, in the expanded configuration, is configured to have interior pressure that corresponds to an applied pressure of 20 cm $H_2O$ or less by an exterior surface of the conformable conduit.

13. A system, comprising:
a tracheal tube comprising:
a conformable conduit forming an airway lumen to transfer respiratory gases to a patient;
a helical inflatable lumen formed in or on an interior surface of the conformable conduit, wherein the helical inflatable lumen forms a spiral about the interior surface, and wherein the inflatable lumen is closed at a first end such that fluid transferred into the inflatable lumen from a second end causes the conformable conduit to assume an expanded configuration to expand an outer diameter of the conformable conduit relative to an unexpanded configuration of the conformable conduit, wherein the helical inflatable lumen terminates in an annulus encircling a distal end of the conformable conduit; and
an inflation controller configured to adjust inflation of the inflatable lumen by transferring inflation fluid to or from the inflatable lumen, the inflation controller comprising a memory and a processor configured to execute instructions stored in the memory, the instructions causing the inflation controller to:
receive a pressure measurement indicative of a pressure of the inflatable lumen; and
adjust the pressure of the inflatable lumen based on the pressure measurement.

14. The system of claim 13, wherein the inflation controller is configured to adjust the pressure to a target pressure, the target pressure being based on a compliance curve for a material forming the inflatable lumen.

* * * * *